United States Patent
Bratkovski et al.

(10) Patent No.: US 9,453,793 B2
(45) Date of Patent: Sep. 27, 2016

(54) INTEGRATED SENSORS

(75) Inventors: Alexandre M Bratkovski, Mountain View, CA (US); R Stanley Williams, Portola Valley, CA (US); Zhiyong Li, Foster City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 536 days.

(21) Appl. No.: 13/452,218

(22) Filed: Apr. 20, 2012

(65) Prior Publication Data

US 2014/0028995 A1  Jan. 30, 2014

(51) Int. Cl.
*G01N 21/00* (2006.01)
*G01N 21/01* (2006.01)
*G01N 21/65* (2006.01)
*G01N 21/64* (2006.01)

(52) U.S. Cl.
CPC ............ *G01N 21/01* (2013.01); *G01N 21/658* (2013.01); *G01N 21/648* (2013.01)

(58) Field of Classification Search
CPC ........................ G01N 21/65; G01N 2021/656
USPC ................ 422/82.05, 82.06, 82.11; 436/164; 356/301
See application file for complete search history.

(56) References Cited

U.S. PATENT DOCUMENTS

| 5,866,430 | A | 2/1999 | Grow |
| 6,174,677 | B1 | 1/2001 | Vo-Dinh |
| 6,565,813 | B1 * | 5/2003 | Garyantes ..................... 422/553 |
| 7,267,948 | B2 | 9/2007 | Vo-Dinh |
| 7,402,531 | B1 | 7/2008 | Kuekes et al. |
| 7,605,916 | B2 | 10/2009 | Zhang et al. |
| 7,662,298 | B2 | 2/2010 | Hersam et al. |
| 7,888,129 | B2 | 2/2011 | Hulteen et al. |
| 8,003,408 | B2 | 8/2011 | Zhang et al. |
| 2002/0195463 | A1 | 12/2002 | Seki et al. |
| 2003/0049563 | A1 | 3/2003 | Iida et al. |
| 2005/0074784 | A1 | 4/2005 | Vo-Dinh |
| 2009/0066934 | A1 | 3/2009 | Gao et al. |

(Continued)

FOREIGN PATENT DOCUMENTS

| CN | 1410155 A | 4/2003 |
| CN | 101460830 | 6/2009 |

(Continued)

OTHER PUBLICATIONS

Ge et al., "Cross-Linked Polymer Replica of a Nanoimprint Mold at 30 nm Half-Pitch", Nano Letters, vol. 5, No. 1, 2005, pp. 179-182.

(Continued)

*Primary Examiner* — Jill Warden
*Assistant Examiner* — Dwayne K Handy
(74) *Attorney, Agent, or Firm* — Dierker & Kavanaugh, P.C (57) ABSTRACT

Examples of integrated sensors are disclosed herein. An example of an integrated sensor includes a flexible substrate, and an array of spaced apart sensing members formed on a surface of the flexible substrate. Each of the spaced apart sensing members includes a plurality of polygon assemblies. The polygon assemblies are arranged in a controlled pattern on the surface of the flexible substrate such that each of the plurality of polygon assemblies is a predetermined distance from each other of the plurality of polygon assemblies, and each of the plurality of polygon assemblies including collapsible signal amplifying structures controllably positioned in a predetermined geometric shape.

17 Claims, 5 Drawing Sheets

(56) References Cited

U.S. PATENT DOCUMENTS

| | | |
|---|---|---|
| 2009/0097022 A1 | 4/2009 | Shen et al. |
| 2009/0103082 A1 | 4/2009 | Black et al. |
| 2009/0321261 A1 | 12/2009 | Vlahovic et al. |
| 2010/0159222 A1 | 6/2010 | Hata et al. |
| 2010/0240144 A1 | 9/2010 | Gilbert |
| 2010/0261280 A1 | 10/2010 | Black et al. |
| 2010/0321684 A1 | 12/2010 | Bratkovski et al. |
| 2011/0116089 A1 | 5/2011 | Schmidt et al. |
| 2011/0267614 A1 | 11/2011 | Reinhard et al. |
| 2012/0105841 A1* | 5/2012 | Hu et al. ............. 356/301 |
| 2012/0212732 A1* | 8/2012 | Santori et al. ............. 356/301 |
| 2013/0040862 A1 | 2/2013 | Li et al. |
| 2013/0278928 A1* | 10/2013 | Mourey et al. ............. 356/301 |

FOREIGN PATENT DOCUMENTS

| | | |
|---|---|---|
| JP | 2002-535646 | 10/2002 |
| JP | 2002-357616 | 12/2002 |
| JP | 2004-045357 | 2/2004 |
| JP | 2010-230352 | 10/2010 |
| JP | 2010230352 A | 10/2010 |
| WO | WO-2011133143 | 10/2011 |
| WO | WO-2011133144 | 10/2011 |

OTHER PUBLICATIONS

Liu et al., "The SERS Response of Semiordered Ag Nanorod Arrays Fabricated by Template Oblique Angle Deposition", J. of Raman Spectroscopy 2010, 41, pp. 1112-1118.

Wu, et al, "Cones Fabricatied by 3D Nanoimprint Lithography for Highly Sensitive Surface Enhanced Raman Spectroscopy", Nanotechnoiogy 21 (2010), 255502, 6 pages.

Wu, et al., "One-Kilobit Cross-Bar Molecular Memory Circuits at 30-nm Half-Pitch Fabricated by Nanoimprint Lithography", Appl. Phys. A 80, 2005, pp. 1173-1178.

Hu, M. et al., "Gold Nanofingers for Molecule Trapping and Detection", Journal of the American Chemical Society, Aug. 26, 2010, vol. 132, No. 37, pp. 12820-12822.

Kim, A. et al., "Study of Molecular Trapping Inside Gold Nanofinger Arrays on Surface-Enhanced Raman Substrates", Journal of the American Chemical Society, Apr. 25, 2011, vol. 133, No. 21, pp. 8234-8239.

PCT International Search Report, Nov. 28, 2012, Application No. PCT/US2012/034448 (filed Apr. 20, 2012).

* cited by examiner

INTEGRATED SENSORS

STATEMENT REGARDING FEDERALLY SPONSORED RESEARCH OR DEVELOPMENT

This invention was made in the course of research partially supported by grants from the Defense Advanced Research Projects Agency (DARPA), Contract No. HR0011-09-3-0002. The U.S. government has certain rights in the invention.

BACKGROUND

Assays and other sensing systems have been used in the chemical, biochemical, medical and environmental fields to detect the presence and/or concentration of one or more chemical species. Some sensing techniques utilize color or contrast for species detection and measurement, including, for example, those techniques based upon reflectance, transmittance, fluorescence, or phosphorescence. Other sensing techniques, such as Raman spectroscopy or surface enhanced Raman spectroscopy (SERS), study vibrational, rotational, and other low-frequency modes in a system. In particular, Raman spectroscopy is used to study the transitions between molecular energy states when photons interact with molecules, which results in the energy of the scattered photons being shifted. The Raman scattering of a molecule can be seen as two processes. The molecule, which is at a certain energy state, is first excited into another (either virtual or real) energy state by the incident photons, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation photons. The Raman spectrum of different molecules or matters has characteristic peaks that can be used to identify the species.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

The present disclosure relates generally to integrated sensors. Examples of the integrated sensors are suitable for use in surface enhanced Raman spectroscopy (SERS). Examples of the sensors include one or more sensing members that include collapsible or reconfigurable signal amplifying structures arranged in polygon assemblies. The collapsible signal amplifying structures of a single polygon assembly are able to undergo self-coalescence (e.g., self-closing or self-reconfiguration at their tips), with the aid of capillary forces (e.g., during liquid evaporation). The signal amplifying structures are able to trap molecules at hot spots formed among the closed tips, which greatly amplifies electromagnetic fields under SERS interrogation. Additionally, examples of the integrated sensor are controllably formed on flexible substrates, which may advantageously be used for continuous monitoring over long periods of time. Still further, some examples of the integrated sensor are able to self-position samples exposed thereto, such that the samples are directed toward the collapsible signal amplifying structures. In these examples, the integrated sensors are able to dynamically reconfigure the samples for optimal signal enhancement.

Figure 1A:
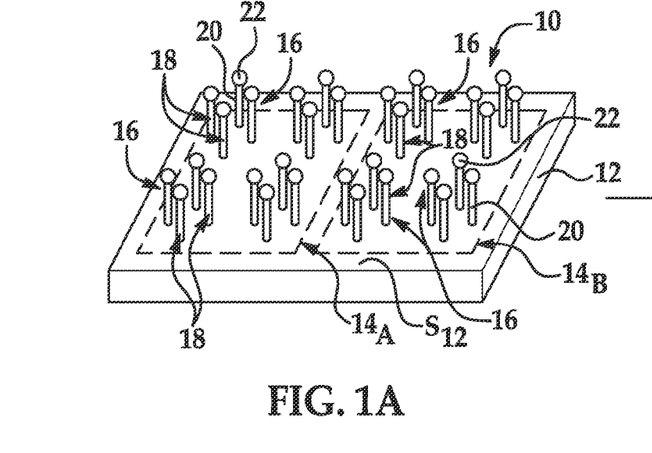
FIGS. 1A and 1B are semi-schematic, perspective views of an example of an integrated sensor prior to and after exposure to a liquid sample.
Figure 1B:
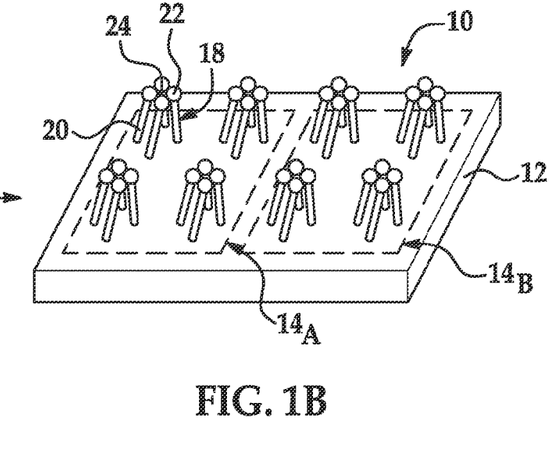

Referring now to FIGS. 1A and 1B, an example of the integrated sensor 10 is depicted prior to liquid sample exposure (FIG. 1A) and after liquid sample exposure (FIG. 1B). In an example, the integrated sensor 10 includes a flexible substrate 12 and an array of spaced apart sensing members $14_A$, $14_B$ formed on the surface $S_{12}$ of the flexible substrate 12. While two sensing members $14_A$, $14_B$ are shown in FIGS. 1A and 1B, it is to be understood that any number of sensing members $14_A$, $14_B$ (also referred to herein as 14) may be formed on the flexible substrate 12. For example, a single sensing member $14_A$ or $14_B$ may be formed, or tens or hundreds of sensing members $14_A$, $14_B$ may be formed. The number of sensing members $14_A$, $14_B$ formed may be limited, for example, by the dimensions (i.e., length and width) of the flexible substrate 12 and/or by the number of polygon assemblies 16 formed in any one sensing member $14_A$, $14_B$. As some examples, the array of sensing members $14_A$, $14_B$ may include a single row of sensing members $14_A$, $14_B$ along a length of the flexible substrate 12 (see, e.g., FIG. 9), or multiple rows along the length of the flexible substrate 12 and multiple columns along a width of the flexible substrate 12 (see, e.g., FIG. 8). The spacing between adjacent sensing members $14_A$, $14_B$ may depend, for example, upon the dimensions (i.e., length and width) of the flexible substrate 12 and/or the configuration of the dispenser, light source, detector, etc. of a sensing system that will be used to interrogate the sensor 10. For example, if the sensing system has a single dispenser for dispensing the analyte solution (i.e., sample) to the sensing members $14_A$, $14_B$, the sensing members $14_A$, $14_B$ may be spaced apart a distance ranging from about 1000 μm (i.e., 1 mm) to about 10000 μm (i.e., 10 mm) from one another in a single row along the length of the flexible substrate 12 so that the dispenser can be actuated to fill the sensing members 14$_A$, 14$_B$ one after the other. In another example, the distance between adjacent sensing members 14$_A$, 14$_B$ ranges from about 200 μm (0.2 mm) to about 500 μm (0.5 mm) or to about 1000 μm (i.e., 1 mm). A single sensing member 14$_A$, 14$_B$ may have a length and/or width ranging from about 0.1 mm to about 2 mm. In an example, a single sensing member 14$_A$, 14$_B$ may have a length and/or width of about 1 mm.

The flexible substrate 12 may be any substrate material that is capable of being flexed or bent without breaking. The flexible substrate 12 is also capable of having signal amplifying structures 18 formed therein. The flexibility may also enable the flexible substrate 12 to be indexed or moved (e.g., in a continuous manner or a ratcheted manner) for monitoring. Examples of the flexible substrate 12 include polyethylene terephthalate (PET), polyethylene terephthalate glycol-modified (PETG), polypropylene, polyethylene, or polycarbonate. In an example, the flexible substrate 12 has a thickness that ranges from about 30 μm to about 50 μm. In other examples, the thickness of the substrate 12 is greater than 50 μm. In examples in which harder materials are used (e.g., polycarbonate), the thickness of the substrate 12 may be at the lower end of the thickness range in order to obtain the desired flexibility. The width of some substrates 12 may range from about 8 mm to about 12 mm.

In the example shown in FIGS. 1A and 1B, each sensing member 14$_A$, 14$_B$ includes a plurality of polygon assemblies 16 arranged in a controlled pattern on the surface S$_{12}$ of the flexible substrate 12. The controlled pattern may include any N×M array, where N, M are individually selected from 2, 3, 4, 5 . . . 50 . . . 2000. In an example, N=M=100 to 1000. The controlled pattern of the polygon assemblies 16 shown in each of the sensing members 14$_A$, 14$_B$ of FIGS. 1A and 1B is a 2×2 array. In this example, each of the sensing members 14$_A$, 14$_B$ has the same controlled pattern, but it to be understood that one or more of the sensing members 14$_A$, 14$_B$ may have the polygon assemblies 16 arranged in a different controlled pattern than one or more of the other sensing members 14$_A$, 14$_B$. Each polygon assembly 16 within a single sensing member 14$_A$ or 14$_B$ may be a predetermined distance from each other polygon assembly 16 within the same sensing member 14$_A$ or 14$_B$. In an example, the predetermined distance may range from about 0.5 μm to about 1 μm, or to about 10 μm. In another example, the predetermined distance may be about 0.7 μm. The controlled pattern and the predetermined distance may be obtained using the fabrication methods disclosed herein.

Figure 2A:
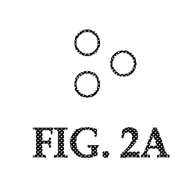
FIGS. 2A through 2E are semi-schematic, top views of five different examples of predetermined geometric shapes of controllably positioned collapsible signal amplifying structures.
Figure 2B:
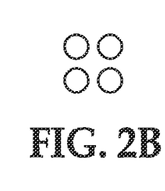
Figure 2C:
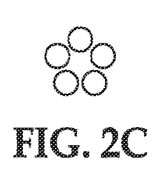
Figure 2D:
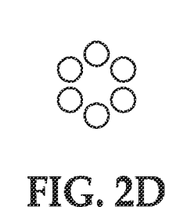
Figure 2E:
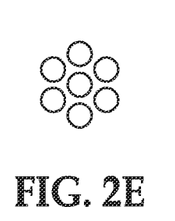

Each polygon assembly 16 includes collapsible signal amplifying structures 18 controllably positioned in a predetermined geometric shape. Top views of examples of the predetermined geometric shapes are shown in FIGS. 2A through 2E. These shapes include trigons (i.e., a 3-mer, including three collapsible signal amplifying structures 18 as shown in FIG. 2A), tetragons (i.e., a 4-mer, including four collapsible signal amplifying structures 18 as shown in FIG. 2B), pentagons (i.e., a 5-mer, including five collapsible signal amplifying structures 18 as shown in FIG. 2C), hexagons (i.e., a 6-mer, including six collapsible signal amplifying structures 18 as shown in FIG. 2D), and heptagons (i.e., a 7-mer, including seven collapsible signal amplifying structures 18 as shown in FIG. 2E). In examples, the period of a polygon assembly 16 having a trigon shape or a tetragon shape ranges from about 400 nm to about 700 nm, and the period of the polygon assembly 16 having a pentagon shape, hexagon shape, or heptagon shape ranges from about 600 nm to about 900 nm. In an example, an array of polygon assemblies 16 in a single sensing member 14$_A$, 14$_B$ may occupy a space on the flexible substrate 12 that is from about 50 μm to about 100 μm wide and from about 50 μm to about 100 μm long. As examples, a 3×3 array of pentagons may cover an area of about 2×2 μm$^2$, while a 30×30 array of pentagons may cover an area of about 20×20 μm$^2$.

It is believed that the controlled fabrication of signal amplifying structures 18 in a predetermined geometric shape has not been achieved, at least in part because of the difficulty in obtaining a desired small gap size (e.g., sub-2 nm gaps between the collapsed signal amplifying structures), while also forming substantially uniform structures of arbitrary symmetry (e.g., tetramers, pentamers, heptamers, etc.) across a large area. However, the fabrication methods disclosed herein enable one to control the collapsed gap size as well as the geometry of the polygon assemblies across a relatively large area (e.g., from about 8 mm to about 12 mm wide).

Figure 3A:
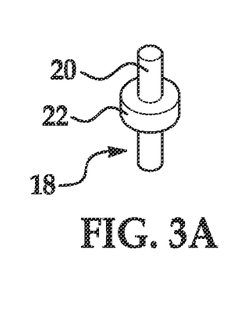
FIGS. 3A through 3C are semi-schematic, perspective views of three different examples of a collapsible signal amplifying structure.
Figure 3B:
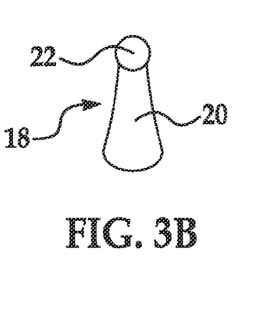

Each collapsible signal amplifying structure 18 includes a polymer base nano-structure 20 and a signal amplifying material 22 positioned thereon. Examples of the polymer base nano-structures 20 include the pillar, columnar, or finger-like structures shown in FIGS. 1A, 1B and 3A, the nanoflake structure shown in FIG. 3B, and the mushroom-shaped nano-structure shown in FIG. 3C. As will be described below in reference to FIGS. 4A through 4D, these polymer base nano-structures 20 are formed in the flexible substrate 12, and thus are formed of the same material as the flexible substrate 12.

The signal amplifying material 22 may be any material that is capable of enhancing the signal that is generated during a particular sensing process. In an example, the signal amplifying material 22 is a Raman signal-enhancing material (composition of matter) that increases the number of Raman scattered photons when the molecule (or other species of interest) is trapped by collapsed signal amplifying structure(s) 18, and when the molecule and materials 22 are subjected to light/electromagnetic radiation. Raman signal-enhancing materials include, but are not limited to, silver, gold, and copper. The signal amplifying material 22 may also be selected for use in other techniques, such as enhanced fluorescence (e.g., metal-enhanced fluorescence or surface enhanced fluorescence (SEF)) or enhanced chemiluminescence. As an example, for metal-enhanced fluorescence applications, the polymer base structures 20 of the signal amplifying structures 18 may be coated with silver nanoparticles. Enhanced fluorescence is observed when incident light couples to the silver nanoparticles with molecules in their vicinity. The signal amplifying material 22 may be configured to couple the localized, and in some instances propagating, surface plasmons. Methods for depositing the signal amplifying material 22 in desirable positions on the polymer base nano-structures 20 to form the collapsible signal amplifying structure 18 will also be discussed in reference to FIGS. 4A through 4D.

As illustrated at the arrow between FIGS. 1A and 1B, each of the sensing members 14$_A$, 14$_B$ of the integrated sensor 10 of FIG. 1A is exposed to a liquid sample. As shown in FIG. 1B, the collapsible signal amplifying structures 18 that are exposed to the sample undergo self-closing with the aid of capillary forces, so that the signal amplifying materials 22 are drawn toward one another to create sub-nm gaps where analytes of interest (e.g., analyte 24) present in the original liquid sample become trapped. As mentioned above, the closed signal amplifying structures 18 form hot spots, which amplify the SERS fields, thereby enhancing the SERS signals.

Referring now to FIGS. 4A through 4D, an example of a method for forming examples of the integrated sensor 10 is semi-schematically depicted. The method is a controlled method based upon nanoimprinting or embossing. FIGS. 4A through 4D describe a method based upon nanoimprinting. Embossing may involve preparing a silicon mold and then using the mold to transfer mold features to a polymer.

Figure 4A:
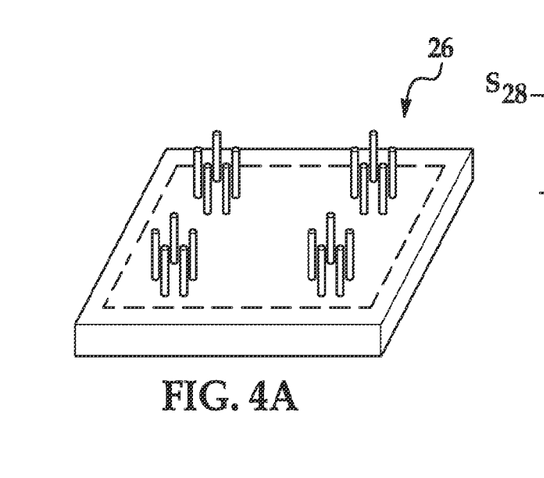
FIGS. 4A through 4D are semi-schematic, perspective views which together illustrate an example of a method for making an integrated sensor, and which also include two cross-sectional views at the arrows between FIGS. 4A and 4B and between FIGS. 4B and 4C.

FIG. 4A illustrates a perspective view of a mold 26 that may be used to form the polygon assemblies 16 of each sensing member $14_A$, $14_B$. The mold 26 shown in FIG. 4A includes a pattern for forming one sensing member having four polygon assemblies, each of which is a pentagon or 5-mer. This is a simplified example of the mold 26, and it is to be understood that the mold 26 may have any controlled pattern(s) that mimics the polygon assemblies to be formed, including the controlled geometric shape of the polymer base nano-structures 20 of the signal amplifying structures 18 to be formed. For example, when multiple sensing members are to be formed using the mold 26, the mold 26 may include a plurality of spaced apart controlled patterns, each of which corresponds to the desired pattern of the respective structures to be formed. The patterns and features of the mold 26 will be used to form the patterns and features of the final integrated sensor 10. The mold 26 may be formed of single crystalline silicon, polymeric materials (acrylics, polycarbonates, polydimethylsiloxane (PDMS), polyimide, etc.), metals (aluminum, copper, stainless steel, nickel, alloys, etc.), quartz, ceramic, sapphire, silicon nitride, or glass.

When multiple sensing members 14, $14_A$, $14_B$ are to be formed, the mold 26 includes a pattern for the to-be-formed sensing members 14, $14_A$, $14_B$ (i.e., defining the spacing between sensing members), a pattern for the placement of the to-be-formed polygon assemblies 16 of each sensing member 14, $14_A$, $14_B$, and a pattern for the to-be-formed polymer base nano-structures 20 of each polygon assembly 16. In other words, the mold patterns are a replica of the desired sensing members 14, $14_A$, $14_B$ (including the polygon assemblies 16) to be formed in the flexible substrate 12.

The patterns may be integrally formed in the mold 26. In an example, the patterns may be formed in the mold 26 via electron-beam (e-beam) lithography or photolithography, and dry etching. To generate the controlled patterns described herein, focused ion-beam or optical lithography may also be used to form the mold 26. The mold may also be prepared by direct etching of a silicon substrate.

Figure 4B:
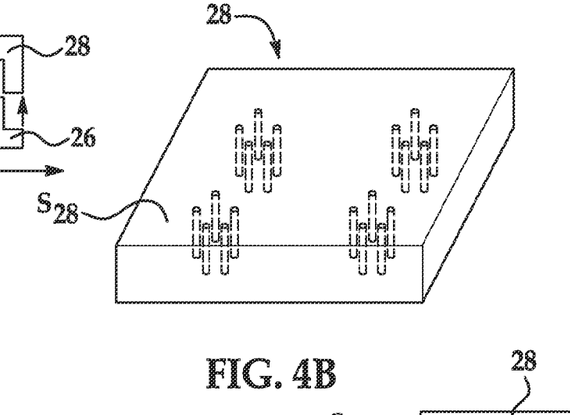
Figure 4C:
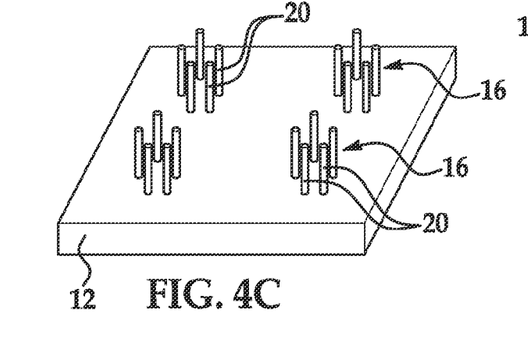

The mold 26 is then used to transfer the controlled patterns to a UV or thermal curable resist to form a polymeric reverse-tone mold 28, which is shown in FIG. 4B. As illustrated, the polymeric reverse-tone mold 28 takes on the negative replica of the patterns of the mold 26. In other words, the controlled pattern of the polygon assemblies and the polymer base nano-structures extend into the surface $S_{28}$ of the polymeric reverse-tone mold 28. As such, the curable resist used to form the polymeric reverse-tone mold 28 is selected to have a sufficient rigidity to be able to conform to, and to duplicate/replicate with precision, the patterns of the mold 26.

Suitable ultraviolet curable resists for forming the polymeric reverse-tone mold 28 include a photoinitiator (i.e., a compound that generates a radical in response to UV radiation exposure), a cross-linking agent, and a siloxane based backbone chain (e.g., a UV-curable acrylated poly(dimethylsiloxane) material). Examples of suitable photoinitiators include azobisisobutyronitrile (AIBN), IRGACURE® 184 and IRGACURE® 810 (commercially available from BASF Corp., Florham Park, N.J.), and examples of the cross-linking agent includes various species having more than one double or triple bond that opens up and polymerizes upon curing. In an example, additional solvents are not included in such UV curable resists, at least in part because of the presence of the siloxane based backbone. The siloxane based backbone may include double bonded terminal functional groups, such as acryls. The components of the UV resist suitable to form the polymeric reverse-tone mold 28 may be included in a predetermined ratio of photoinitiator to cross-linking agent to siloxane backbone. Each component can be present in a range of 0.05% to 99.9% of the total weight of the resist. In an example, the UV resist includes from about 0.5 wt % to about 2 wt % of the radical initiator, from about 88 wt % to about 92 wt % of the UV curable monomer species (i.e., the siloxane based backbone chain), and from about 7 wt % to about 11 wt % of the cross-linking agent. In another example, the UV resist includes 1 wt % of the radical initiator, 90 wt % of the UV curable monomer species (i.e., the siloxane based backbone chain), and 9 wt % of the cross-linking agent. Commercially available resists that may be used for the curable resist include NXR-2010 (Nanonex Corp., Monmouth Junction, N.J.), and AR-UV-01 (Nanolithosolution, Inc., San Marcos, Calif.).

In an example, the polymeric reverse-tone mold 28 may be formed using ultraviolet-curable (i.e., UV-curable) nanoimprint lithography (NIL). A UV-capable NIL tool may be used in this process. The previously described UV curable resist may be deposited (e.g., via spin coating, drop coating, dip-coating, or the like) onto the mold 26, and then may be cured (in the tool) to form the polymeric reverse-tone mold 28. In another example, the mold 26 may be pressed into the resist that had been previously deposited on a substrate, and then curing is performed. It is to be understood that the curing conditions and parameters will depend, at least in part, on the UV resist that is used. It is to be further understood that while the mold 26 is pressed into (or otherwise in contact with) the resist, partial curing may be performed. Partial curing cures some, but not all, of the resist. After partial curing, the mold 26 may be removed. Once the mold 26 is removed, curing may be continued until the resist is fully cured to form the polymeric reverse-tone mold 28.

Prior to depositing the UV curable resist onto the mold 26 or prior to pressing the mold 26 into the UV curable resist, the mold 26 may be primed with a chlorosilane coupling agent (e.g., 3-acryloxypropyl)methyldichlorosilane) that aids in removal of the polymeric reverse-tone mold 28 from the mold 26 after curing is complete. The cross-sectional view shown at the arrow between FIGS. 4A and 4B illustrates the polymeric reverse-tone mold 28 being removed from the mold 26.

The polymeric reverse-tone mold 28 may then be used in another UV-curable nanoimprint lithography process (e.g., using the UV-capable NIL tool) to form the polygon assemblies 16 and the associated polymer base nano-structures 20 in the flexible substrate 12. In this example, the polymeric reverse-tone mold 28 may be pressed into the flexible substrate 12 (as shown at the arrow between FIGS. 4B and 4C), and then curing may be performed. After curing is complete, the polymeric reverse-tone mold 28 may be removed, leaving the flexible substrate 12 controllably patterned with polygon assemblies 16 of polymer base nano-structures 20, and thus the sensing members 14.

Figure 4D:
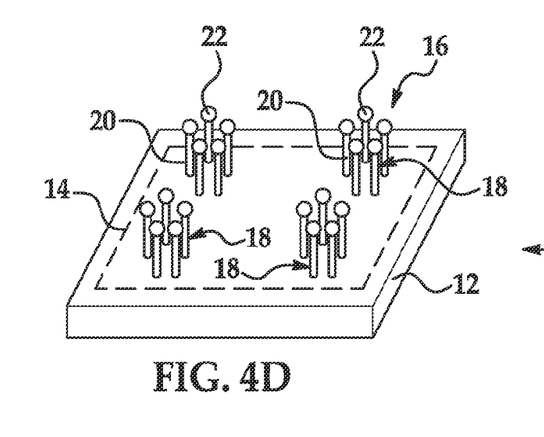

As shown in FIG. 4D, the signal amplifying material 22 is deposited on at least a surface of the polymer base nano-structures 20 to form the signal amplifying structure(s) 18. The signal amplifying material 22 may be established by any suitable deposition or other coating technique. In some examples, a selective deposition technique may be used so that the material 22 is established on, for example, the tips of the base nano-structures 20 alone. As examples, the material 20 may be deposited via electron-beam (e-beam) evaporation at normal incidence, or sputtering. In still other examples, the signal amplifying material 22 can be pre-formed nanoparticles (e.g., of silver, gold, copper, etc.), which are coated onto the polymer base nano-structures 20. Such nanoparticles may have an average diameter ranging from about 5 nm to about 50 nm. It is believed that the presence of the material 22 at the apex or tip of the polymer base nano-structures 20 further enhances the electric field during, e.g., a SERS operation. The material 22 itself may also have a surface roughness that spontaneously forms during the deposition process. This surface roughness can act as additional optical antennas to increases the SERS-active sites over each signal amplifying structure 18. In an example, a thickness of the signal amplifying material 22 ranges from about 50 nm to about 80 nm.

In the method(s) disclosed herein, since the patterns are precisely defined in the original mold 26 (e.g., by the initial e-beam lithography) and are faithfully reproducible by nanoimprint lithography, any array of sensing members 14, $14_A$, $14_B$ having any controlled pattern of polygon assemblies 16 can be fabricated uniformly at desirable positions in the flexible substrate 12.

Figure 3C:
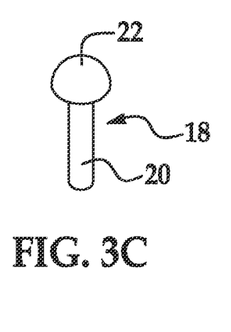

While the method(s) described in reference to FIGS. 4A through 4D illustrates the formation of metal-capped polymer nano-pillars (e.g., signal amplifying structures 18), it is to be understood that the method(s) may also be used to form metal-ringed polymer nano-pillars (shown in FIG. 3A), metal-coated polymer nanoflakes (shown in FIG. 3B), or metal-coated mushroom-shaped nano-structures (shown in FIG. 3C). To form the metal-ringed polymer nano-pillars, for example, selective deposition (e.g., angled deposition) or shadow masking may be used to deposit the signal amplifying material 22 (e.g., preformed material) in the desired position along the height of the pillar 20. In other examples, the metal-ringed polymer nano-pillars may form spontaneously when the signal amplifying material 22 is deposited. To form the polymer nanoflakes or mushroom-shaped nano-structures, the original silicon mold 26 would be formed in these shapes, as opposed to the pillar shape previously described. It is to be understood that these nanoflakes or mushroom-shaped nano-structures may be formed in any of the predetermined geometric shapes (e.g., trigon, tetragon, etc.) to create the polygon assemblies 16 of the sensing members $14_A$, $14_B$.

It is to be understood that the previously described method(s) may be implemented as a roll-to-roll process. It is to be further understood that the previously described methods may also be modified for thermal imprinting (e.g., using a thermal curable resist) or an embossing process.

Figure 5:
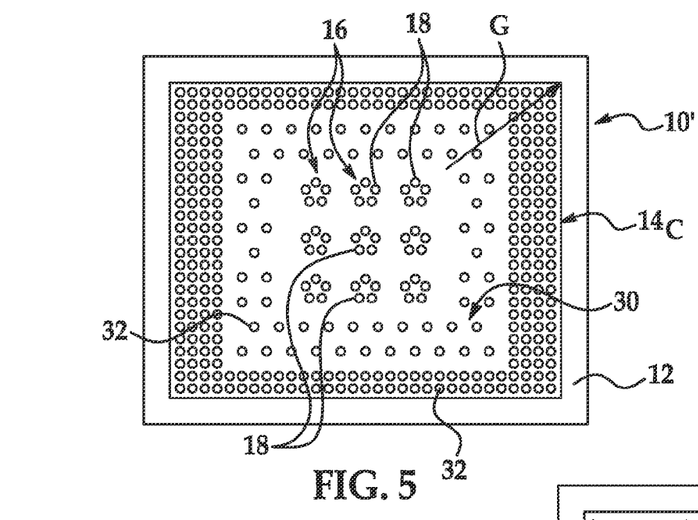
FIG. 5 is a semi-schematic, top view of a sensing member including collapsible signal amplifying structures surrounded by a gradient of polymer nano-pillars.
Figure 6:
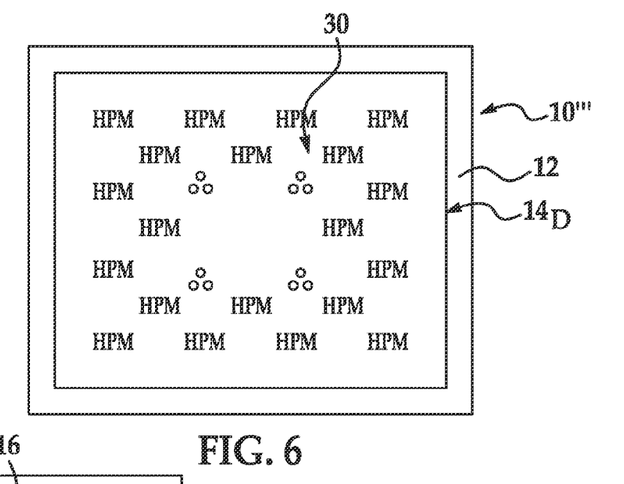
FIG. 6 is a semi-schematic, top view of a sensing member including collapsible signal amplifying structures surrounded by hydrophobic molecules.
Figure 7:
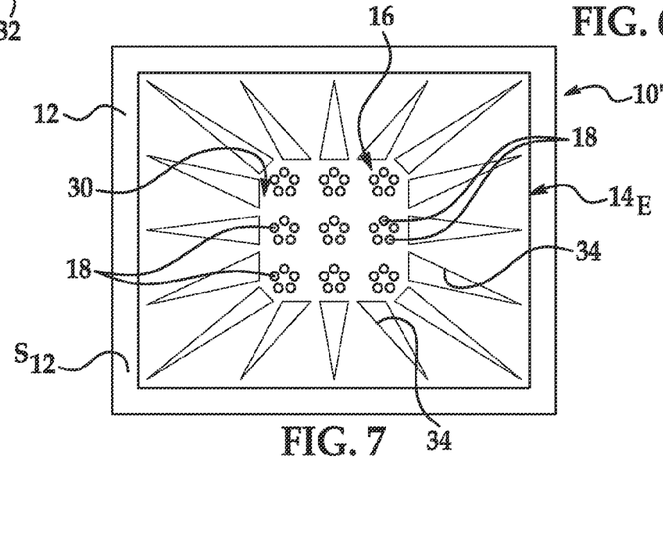
FIG. 7 is a semi-schematic, top view of a sensing member including collapsible signal amplifying structures surrounded by grooves.

Referring now to FIGS. 5 through 7, the integrated sensors 10', 10", and 10''' includes different examples of the sensing members, respectively shown as $14_C$, $14_D$, $14_E$ in these figures. Each of these sensing members $14_D$, $14_D$, $14_E$ includes an area 30 surrounding the collapsible signal amplifying structures 18 that has been modified to enable droplets exposed thereto to position themselves toward the collapsible signal amplifying structures 18. In other words, the area 30 within a sensing member $14_C$, $14_D$, $14_E$ and surrounding the controlled pattern of polygon assemblies 16 of that sensing member 14 may have its surface modified to guide droplets toward the collapsible signal amplifying structures 18. When the droplets reposition themselves at the collapsible signal amplifying structures 18, analytes within the droplets do not get stuck in the area 30 outside of or surrounding the collapsible signal amplifying structures 18, and thus are not unaccounted for during sensing. Rather, the droplets are present at the area of the sensing member $14_C$, $14_D$, $14_E$ that contains the collapsible signal amplifying structures 18. As such, when the droplets evaporate down in size (e.g., to about 50 μm to about 100 μm in diameter), the concentration of the analyte at the polygon assemblies 16 is increased compared to the initial fluid sample.

As will be described further in reference to FIGS. 5 through 7, the modifications made to the area 30 may be chemical and/or physical.

In the examples shown in FIGS. 5 and 6, the wettability of the area 30 is modified. More particularly, the area 30 is modified to be more hydrophobic (i.e., less hydrophilic) than the collapsible signal amplifying structures 18.

In FIG. 5, the area 30 includes a gradient G of polymer pillars with varying separation between the pillars along the gradient G. As illustrated in FIG. 5, the gradient G includes polymer pillars 32 that become denser toward the periphery of the sensing member $14_C$. The gradient G of polymer pillars 32 may be a linear density grade towards the collapsible signal amplifying structures 18 so that droplets exposed to the area 30 move from the periphery of the gradient G toward the collapsible signal amplifying structures 18. The gradient G in FIG. 5 includes two different separation sizes (i.e., gaps) between the pillars 32, but it is to be understood that the separation size between the pillars 32 may vary more than two times along the gradient G. The pillars 32 may have a minimum diameter of about 50 nm, which can be scaled up to about 500 nm in a piece-wise linear manner. The 50 nm diameter pillars 32 may be separated by a distance ranging from about 50 nm to about 150 nm, and the 500 nm diameter pillars 32 may be separated by a distance ranging from about 300 nm to about 500 nm. The scaled up diameters may be anywhere from about 50 nm to about 500 nm, with the distances between these pillars also ranging from about 50 nm to about 500 nm.

The polymer pillars 32 in the area 30 are also free of the signal amplifying material 22.

The polymer pillars 32 may be formed using a mold with the gradient texture, which can transfer the desired pillar gradient to the area 30.

In FIG. 6, the area 30 is chemically modified by depositing or otherwise adding a plurality of hydrophobic molecules HPM to the area 30. Any hydrophobic molecules HPM may be selected, as long as they are more hydrophobic than the collapsible signal amplifying structures 18. Some examples of the hydrophobic molecules HPM may include $(C_2F_2)_n$ chains (e.g., TEFLON®, from DuPont).

In FIG. 7, the area 30 is physically modified with capillary guides or grooves 34 formed into the surface $S_{12}$ of the flexible substrate 12. The capillary guides or grooves 34 may be embossed into the surface $S_{12}$ in the area 30. The shape and dimensions of the capillary guides or grooves 34 is selected so that when a droplet is exposed to the capillary guide or groove 34, the droplet automatically moved toward the collapsible signal amplifying structures 18. In an example, the capillary guide or groove 34 is a fraction of a mm long V-groove with a maximum depth of 10 μm, where the depth becomes linearly more shallow away from the collapsible signal amplifying structures 18.

In other examples of the integrated sensor that are not shown, the area 30 may include both hydrophobic molecules HPM and capillary guides or grooves 34, or both hydrophobic molecules HPM and a polymer pillar gradient G.

In any of the examples disclosed herein, droplet mobility may be increased by heating the sensor 10, 10', 10'', 10''' or by applying a low-power ultrasound. Heating may be accomplished using an external heater, or heat from a SERS light source (e.g., reference number 38 in FIGS. 8 and 9) may be suitable for increasing droplet mobility. Low-power ultrasound may be applied using an integrated Si-based PZT (($PbZr_xTi_{1-x}$)$O_3$) ultrasound transducer. In an example, the ultrasound transducer may be integrated into a silicon substrate. For example, piezoelectric elements may be formed by the deposition of PZT into etched features of the silicon substrate. The ultrasound transducer may be operably positioned as a fixed element between the dispenser 36 and the light source 38. When the substrate 12 is moved during a sensing operation, the ultrasound transducer may be operated to excite a sample that has been dispensed from dispenser 36.

Figure 8:
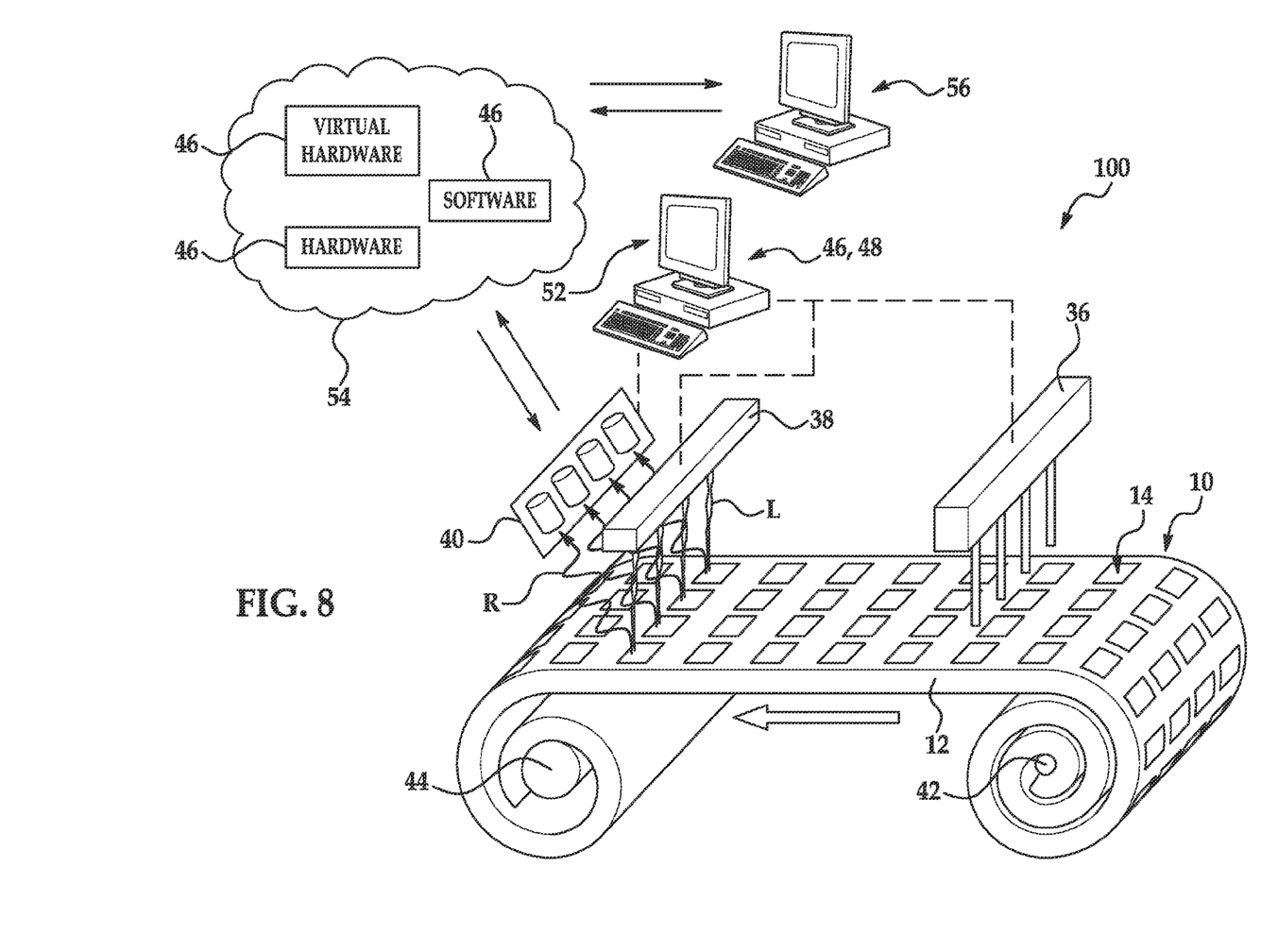
FIG. 8 is a semi-schematic and partially perspective view of an example of a sensing system.

Referring now to FIG. 8, an example of the sensing system 100 incorporating an example of the integrated sensor 10 is depicted. This example of the sensor 10 includes multiple sensing members 14 formed in four columns along the width of the flexible substrate 12 and multiple rows along the length of the flexible substrate 12. While not shown for clarity, it is to be understood that each of the sensing members 14 includes a controlled pattern of polygon assemblies 16, and may include a modified area 30 as described in reference to FIG. 5, 6 or 7.

In the system 100, the flexible substrate 12 is positioned with respect to the components (e.g., dispenser or dispensing system 36, laser source 38, and detector 40) of the sensing system 100 so that dispensing, interrogation, and detection can take place in the desirable order while the flexible substrate 12 is indexed past the respective components 36, 38, and 40. For example, the flexible substrate 12 may be positioned with respect to the dispenser 36 so that one or more samples are introduced onto the sensing member(s) 14 prior to interrogation and detection. The dispensing system 36 may dispense samples to one or more of the sensing members simultaneously (e.g., each member 14 in a single row may receive a sample simultaneously) and/or sequentially (e.g., one sensing member 14 receives a sample at a time, or one row receives a sample at a time, etc.). Examples of the dispensing system 36 include automated dispensers based upon inkjet technology, pipetting, or the like. Manual dispensers may also be used. It is to be understood that the dispensing system 36 may be operable to dispense the same solution to all sensing members 14, or different solutions to two or more of the sensing members 14.

The laser source 38 may be a light source that has a narrow spectral line width, and is selected to emit monochromatic light beams L within the visible range or within the near-infrared range. The laser source 38 is positioned downstream from where the dispensing system 36 is located in the direction that the flexible substrate 12 is indexed. The positioning of the light source 38 with respect to the dispensing system 36 may be far enough to enable dispensed droplets to begin evaporation, while being close enough to supply heat to increase droplet mobility. For example, the laser source 38 may supply heat to the substrate 12 and droplets, thereby facilitating heating up of the droplet, drying of the droplet, and subsequent pillar collapsing due to capillary forces produced by wetting the surface of the polygon assemblies 16. The laser source 38 may be selected from a steady state laser or a pulsed laser. The laser source 32 is positioned to project the light L onto the various sensing members 14. The example shown in FIG. 8 is a VCSEL (vertical cavity surface emitting light) array that exposes an entire row of sensing members 14 to be exposed to light L simultaneously. In other examples, the laser source 38 may be selected to interrogate a single sensing member 14 at a time, or multiple rows of sensing members 14 at the same time. As such, parallel sensing may be performed. A lens (not shown) and/or other optical equipment (e.g., optical microscope) may be used to direct (e.g., bend) the laser light L in a desired manner. In one example, the laser source 38 is integrated on a chip. The laser source 38 may also be operatively connected to a power supply (not shown).

During operation of the system 100, flexible substrate 12 may be indexed from a distribution point 42 to a receiving point 44. As the flexible substrate 12 is indexed, the dispensing system 36 may be operated to dispense one or more samples (containing analyte(s) of interest) into desired sensing members 14. The dispensing system 36 may be programmed to dispense into each row, every other row, or in any other desirable configuration.

As the flexible substrate 12 is indexed, the dispensed samples begin to evaporate, thereby collapsing the signal amplifying structures 18 within each sensing member 14 that has been exposed to a sample, and capturing analytes in the collapsed structures. When sensing members 14 that have received samples are adjacent to the light source 38, the laser source 38 is operated to emit light L toward the respective sensing members 14. The analyte molecules trapped in or concentrated at or near the signal amplifying structures 18 of the sensing members 14 interact with and scatter the light/electromagnetic radiation L (note that the scattered light/electromagnetic radiation is labeled R). The interactions between the analyte molecules and the signal amplifying material 22 (shown in FIG. 8) of the signal amplifying structures 18 cause an increase in the strength of the Raman scattered radiation R. The Raman scattered radiation R is redirected toward the photodetector 40, which may optically filter out any reflected components and/or Rayleigh components and then detect an intensity of the Raman scattered radiation R for each wavelength near the incident wavelength.

Indexing of the flexible substrate 12 may be continuous so that the SERS analysis occurs without interruption for a desired period of time, or it may be pulsed so that indexing and SERS analysis takes place for a predetermined time, followed by another predetermined time where no indexing and no SERS analysis takes place. The electronics operating the sensing system 100 may be programmed to perform the desired continuous or periodic monitoring. The sensing system 100 could be used to perform a sensing operation on demand.

Additionally, as shown in FIG. 8, the system 100 and sensor 10 allow for dispensing into one row to take place while interrogation and detection take place in another row that already received a dispensed sample. This configuration allows contributes to the ability for continuous monitoring to take place. While not shown, it is to be understood that the system 100 may include an electronic mechanism or a mechanical mechanism that rotates the distribution point (e.g., spool) 42 to release additional flexible substrate 12 and unused sensing members 14 while the receiving point (e.g., spool) 44 rotates in the same direction to wind up the spent portion of the integrated sensor 10. In one example, the continuous homogeneous indexing is performed. In another example, during indexing headers of new datasets may be written with some cataloguing information.

While not shown, it is to be understood that the system 100 may include a light filtering element positioned between the sensing members 14 and the photodetector 40. This light filtering element may be used to optically filter out any Rayleigh components, and/or any of the Raman scattered radiation R that is not of a desired region. The system 100 may also include a light dispersion element positioned between the sensing members 14 and the photodetector 40. The light dispersion element may cause the Raman scattered radiation R to be dispersed at different angles. The light filtering and light dispersion elements may be part of the same device or may be separate devices.

Hardware 46, 46', programming 48, or combinations thereof may also be operatively connected to the dispensing system 36, the laser source 38 and the photodetector 40 to control these components 36, 38, 40. While not shown, hardware 46, 46' and/or programming 48 may also be operatively connected to the distribution point 42 and the receiving point 44 in order to cause the movement of the integrated sensor 10.

The same or different hardware 46, 46' may receive readings from the photodetector 40, and cause the same or different associated programming 48 to produce a Raman spectrum readout, the peaks and valleys of which are then utilized for analyzing the analyte molecules. The hardware 46, 46' may include memory device(s) that can store data transmitted thereto for subsequent retrieval, analysis, review, creation of a library or database, etc.

The hardware 46 and/or programming 48 may be part of a device 52 that is directly connected to the components 36, 38, 40. Additionally or alternatively, hardware 46 and/or programming 48 may be part of a cloud computing system 54. Local hardware 46 and/or associated programming 48 may be desirable to operate the dispensing system 36, the laser source 38 and the photodetector 40, and the cloud computing system 54 may be desirable for data storage and performing applications with such data.

The cloud computing system 54 is a computing system that includes multiple pieces of hardware 46, 46' operatively coupled over a network so that they can perform a specific computing task (e.g., running the system 100 components, receiving data from the detector 40, enabling a user to access and/or manipulate stored SERS data, statistical information, etc., and/or enabling a user to perform pre- and post-data processing, anomaly detection, trend emergence/breakdown, jumps in the data, etc.). The cloud hardware may include a combination of physical hardware 46 (e.g., processors, servers, memory, etc.), software (i.e., associated programming 48), and virtual hardware 46'. In an example, the cloud 54 may be configured to (i) receive requests from a multiplicity of users through application client devices 56, and (ii) return request responses. In the examples disclosed herein, the requests may relate to retrieval of SERS data, building of a SERS library utilizing the user's stored data, etc.

Physical hardware 46 may include processors, memory devices, and networking equipment. Virtual hardware 46' is a type of software that is processed by physical hardware 46 and designed to emulate specific software. For example, virtual hardware 46' may include a virtual machine, i.e. a software implementation of a computer that supports execution of an application like a physical machine. An application, as used herein, refers to a set of specific instructions executable by a computing system for facilitating carrying out a specific task. For example, an application may take the form of a web-based tool providing users with a specific functionality, e.g., retrieving previously saved SERS data. Software 48 is a set of instructions and data configured to cause virtual hardware 46' to execute an application. As such, the cloud 54 can make a particular application related to the sensing system 100 available to users through client devices 56.

The combinations of hardware 46, 46' and programming 48 may be implemented in a variety of fashions. For example, the programming 48 may be processor executable instructions stored on tangible, non-transitory computer readable memory media, and the hardware 46 may include a processor for executing those instructions. The memory media (e.g., hard drive, memory maintained by a server, portable medium such as a CD, DVD, or flash drive, etc.), may be used to store the instructions that, when executed by the processor, allow a user to access data sent to the memory media from the detector 40. In an example, the memory media is integrated in the same device as the processor, or it may be separate from, but accessible to that device and processor.

Figure 9:
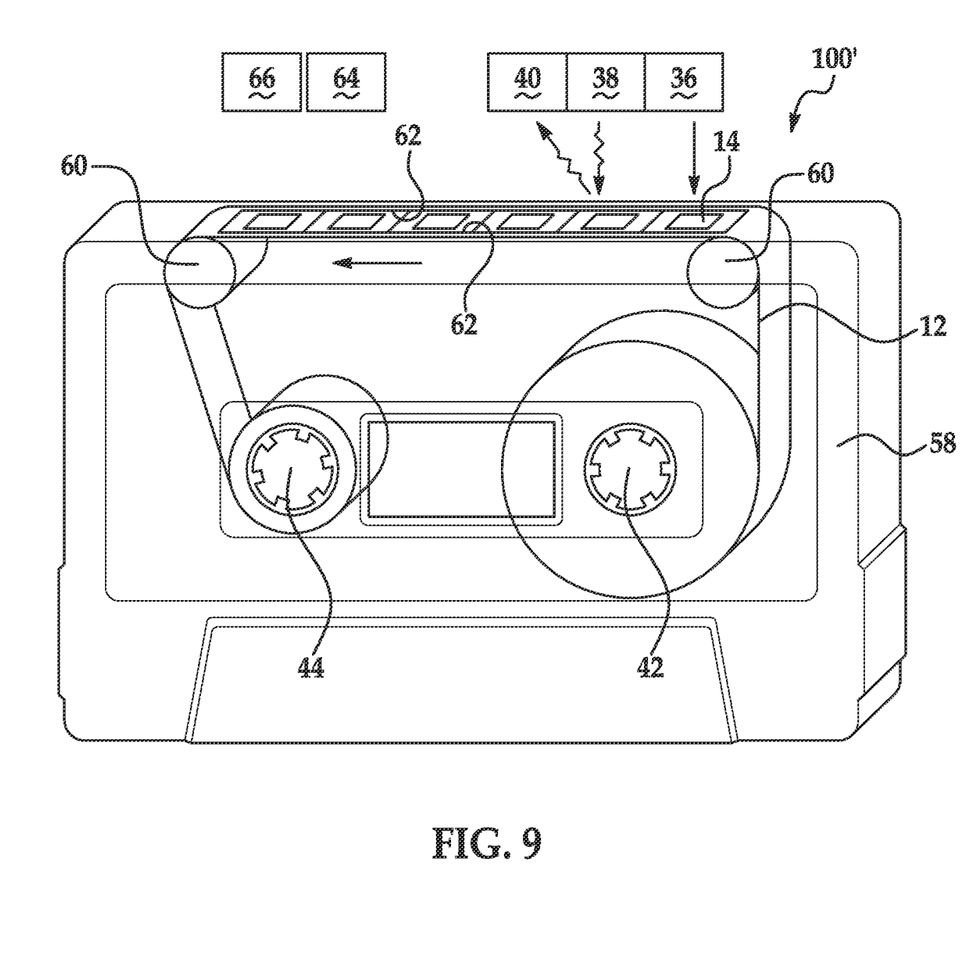
FIG. 9 is a schematic and partially perspective view of another example of a sensing system.

Referring now to FIG. 9, another example of the sensing system 100' is depicted. In this example, the integrated sensor 10 is incorporated into a cassette 58. The cassette 58 includes a housing that contains the integrated sensor 10 therein. The housing may be formed of any suitable material, including, for example, a polymeric material.

The cassette 58 also includes the distribution point/spool 42 and the receiving point/spool 44 therein. The integrated sensor 10 is initially wound on the distribution point/spool 42 and is also attached to the receiving point/spool 44. Upon being indexed, the integrated sensor 10 moves from the distribution point 42 to the receiving point 44. The cassette may also include rollers 60 that assist in the indexing of the flexible substrate 12 from the distribution point/spool 42 to the receiving point/spool 44 during operation. The cassette 58 may include holes in the housing that enable respective rotating prongs to engage the distribution point/spool 42 and the receiving point/spool 44 in order to advance the flexible substrate 12 from the distribution point/spool 42 to the receiving point/spool 44.

The cassette 58 may also include an aperture 62 formed therein. The apertures 62 are formed in one side of the housing to expose the indexed flexible substrate 12 and the sensing members 14 formed thereon to the various components, e.g., 36, 38, 40, etc. of the sensing system 100' as the integrated sensor 10 is indexed. One aperture 62 may be included that is large enough to expose the desirable number of sensing members 14, or, as shown in FIG. 9, multiple apertures 62 may be formed across from the respective components 36, 38, 40, etc. of the sensing system 100'.

While not shown, it is to be understood that the sensing system 100' itself may including a housing with a slot to receive the cassette 58 and to move the cassette 58 into and out of the operating position. Such a housing of the system 100' may also include mechanical and/or electrical components to advance the integrated sensor 10 in the proper manner and initiate, for example, the dispensing system 36, the laser source 38, and the detector 40 when it is desirable to perform a sensing operation.

As described in reference to FIG. 8, the dispenser 36, laser source 38, and detector 40 are positioned to dispense, then interrogate and detect in that order. While not shown, it is to be understood that this sensing system 100' may also include the hardware 46, 46' and associated programming 48 for operating the components of the system 100' and/or storing data received from the detector 40.

This example of the sensing system 100' also includes other systems, such as a pressure sensing system 64 and a temperature analysis system 66. The pressures sensing system 64 measures the pressure of the system 100' and the temperature analysis system 66 measures the temperature of the system 100'. The pressure sensing system 64 and/or the temperature analysis system 66 is a separate unit to measure environmental characteristics complementary to the measurements taken by the SERS components. It is believed that other sensing systems may be included, such as a flow sensor to help debug system errors, for example, dispenser 36 malfunction. It is to be understood that these additional systems are integrated into the sensing system 100' as separate components in addition to the SERS components (e.g., dispenser 36, laser source 38, detector 40). They may be useful to perform other desirable processes in addition to SERS. It is to be understood that these additional sensors may be operatively coupled to whatever hardware 46, 46' and associated programming 48 is utilized to operate the system 100'.

The integrated sensors 10, 10', 10'', and 10''' disclosed herein may be used to perform continuous or periodic monitoring of one sample or multiple samples. The controlled patterns of polygon assemblies 16 within each sensing member 14 on the flexible substrate 12 provides, over a large area, unique signal amplifying structures 18 that are capable of trapping analytes in hot spots to enhance SERS fields and signals.

It is to be understood that the ranges provided herein include the stated range and any value or sub-range within the stated range. For example, a range from about 400 nm to about 600 nm should be interpreted to include not only the explicitly recited limits of about 400 nm to about 600 nm, but also to include individual values, such as 415 nm, 480 nm, 550 nm, etc., and sub-ranges, such as from about 425 nm to about 500 nm, from about 450 nm to about 575 nm, etc. Furthermore, when "about" is utilized to describe a value, this is meant to encompass minor variations (up to +/−10%) from the stated value.

While several examples have been described in detail, it will be apparent to those skilled in the art that the disclosed examples may be modified. Therefore, the foregoing description is to be considered non-limiting.

What is claimed is:

1. An integrated sensor, comprising:
a flexible substrate; and
an array of spaced apart sensing members formed on a surface of the flexible substrate, each of the spaced apart sensing members including a plurality of polygon assemblies arranged in a controlled pattern on the surface of the flexible substrate such that each of the plurality of polygon assemblies is a predetermined distance from each other of the plurality of polygon assemblies, and each of the plurality of polygon assemblies including collapsible signal amplifying structures controllably positioned in a predetermined geometric shape;
wherein the flexible substrate is chosen from polyethylene terephthalate, polyethylene terephthalate glycol-modified (PETG), polycarbonate, polypropylene, and polyethylene, and a thickness of the flexible substrate ranges from about 30 μm to about 50 μm.

2. The integrated sensor as defined in claim 1 wherein the predetermined geometric shape is a trigon, a tetragon, a pentagon, a hexagon, or a heptagon.

3. The integrated sensor as defined in claim 1 wherein the controlled pattern of the plurality of polygon assemblies includes an N×M array of the polygon assemblies, wherein N and M are individually chosen from 2 to 2000.

4. The integrated sensor as defined in claim 1 wherein the collapsible signal amplifying structures include metal-capped polymer nano-pillars, metal-coated polymer nano-flakes, metal-coated mushroom-shaped nano-structures, or metal-ringed polymer nano-pillars.

5. The integrated sensor as defined in claim 1 wherein the array of sensing members includes i) a single row of sensing members along a length of the flexible substrate, or ii) multiple rows along the length of the flexible substrate and multiple columns along a width of the flexible substrate.

6. A sensing system, comprising:
the integrated sensor as defined in claim 1;
a sensing device to receive the integrated sensor and to index the flexible substrate from a distribution point to a receiving point, the sensing device, including:
a dispensing system to dispense a sample on at least one of the sensing members as the flexible substrate is indexed;
a laser source to project light onto the at least one of the sensing members after it has been exposed to the sample;
a detector to detect a signal emitted after the at least one of the sensing members has been exposed to the light; and
a processor operatively connected to the detector.

7. The sensing system as defined in claim 6 wherein the processor is a component of a cloud computing system.

8. The sensing system as defined in claim 6, further comprising any of:
a pressure sensing system to measure a pressure of the sample on the at least one of the sensing members as the flexible substrate is indexed; or
a temperature analysis system to measure a temperature of the sample on the at least one of the sensing members as the flexible substrate is indexed.

9. An integrated sensor, comprising:
a flexible substrate;
an array of spaced apart sensing members formed on a surface of the flexible substrate, each of the spaced apart sensing members including a plurality of polygon assemblies arranged in a controlled pattern on the surface of the flexible substrate such that each of the plurality of polygon assemblies is a predetermined distance from each other of the plurality of polygon assemblies, and each of the plurality of polygon assemblies including collapsible signal amplifying structures controllably positioned in a predetermined geometric shape;
a housing including at least one aperture;
a distribution spool operatively positioned within the housing, the distribution spool having the flexible substrate wound thereon; and
a receiving spool operatively positioned within the housing to receive the flexible substrate from the distribution spool;
wherein the flexible substrate is to be indexed past the at least one aperture such that the array of sensing members is accessible through the at least one aperture.

10. An integrated sensor, comprising:
a flexible substrate; and
an array of spaced apart sensing members formed on a surface of the flexible substrate, each of the spaced apart sensing members including:
a plurality of polygon assemblies arranged in a controlled pattern on the surface of the flexible substrate such that each of the plurality of polygon assemblies is a predetermined distance from each other of the plurality of polygon assemblies, and each of the plurality of polygon assemblies including collapsible signal amplifying structures controllably positioned in a predetermined geometric shape; and an area defined by a periphery and surrounding the plurality of polygon assemblies, the area having been modified to enable a droplet exposed thereto to reposition itself toward the collapsible signal amplifying structures of the plurality of polygon assemblies, wherein the area includes a physical gradient that causes the droplet to reposition itself toward the collapsible signal amplifying structures, wherein the physical gradient includes a gradient of polymer pillars with varying separation between the polymer pillars along the gradient of polymer pillars, and wherein the gradient of polymer pillars is denser toward the periphery of the area.

11. The integrated sensor as defined in claim 10 wherein the area is chemically modified with a plurality of hydrophobic molecules to make the area more hydrophobic than the collapsible signal amplifying structures.

12. An integrated sensor, comprising:
a flexible substrate; and
an array of spaced apart sensing members formed on a surface of the flexible substrate, each of the spaced apart sensing members including:
a plurality of polygon assemblies arranged in a controlled pattern on the surface of the flexible substrate such that each of the plurality of polygon assemblies is a predetermined distance from each other of the plurality of polygon assemblies, and each of the plurality of polygon assemblies including collapsible signal amplifying structures controllably positioned in a predetermined geometric shape; and
an area defined by a periphery and surrounding the plurality of polygon assemblies, the area having been modified to enable a droplet exposed thereto to reposition itself toward the collapsible signal amplifying structures of the plurality of polygon assemblies, wherein the area includes a physical gradient that causes the droplet to reposition itself toward the collapsible signal amplifying structures, wherein the area is physically modified with capillary guides or grooves, the capillary guides or grooves having a depth that becomes linearly more shallow away from the collapsible signal amplifying structures, toward the periphery of the area.

13. The integrated sensor as defined in claim 12 wherein the area is chemically modified with a plurality of hydrophobic molecules to make the area more hydrophobic than the collapsible signal amplifying structures.

14. A method for using an integrated sensor, the method comprising:
inserting the integrated sensor into a sensing device, the integrated sensor including:
a flexible substrate; and
an array of spaced apart sensing members formed on a surface of the flexible substrate, each of the spaced apart sensing members including a plurality of polygon assemblies arranged in a controlled pattern on the surface of the flexible substrate such that each of the plurality of polygon assemblies is a predetermined distance from each other of the plurality of polygon assemblies, and each of the plurality of polygon assemblies including collapsible signal amplifying structures controllably positioned in a predetermined geometric shape;
operating the sensing device such that the flexible substrate is indexed;
as the flexible substrate is indexed, exposing at least one of the sensing members to a sample;
as the flexible substrate continues to be indexed, performing a sensing operation on the sample that has been exposed to the at least one of the sensing members;
continuously advancing the flexible substrate;
periodically exposing other sensing members to an other sample; and
periodically performing a sensing operation on the other sample that has been exposed to the other sensing members.

15. A method for making an integrated sensor, comprising:
creating a mold having a pattern for an array of to-be-formed spaced apart sensing members and a controlled pattern of a plurality of polygon assemblies for each of the to-be-formed spaced apart sensing members, each of the polygon assemblies including mold-material nano-pillars positioned in a predetermined geometric shape;
transferring the controlled pattern to a polymeric reverse-tone mold using nano- imprinting;
nano-imprinting a flexible substrate using the polymeric reverse-tone mold, thereby forming an array of spaced apart sensing members, each of the spaced apart sensing members including a second plurality of polygon assemblies arranged in the controlled pattern on the surface of the flexible substrate such that each of the second plurality of polygon assemblies is a predetermined distance from each other of the second plurality of polygon assemblies, and each of the polygon assemblies including collapsible nano-pillars controllably positioned in the predetermined geometric shape, wherein the flexible substrate is chosen from polyethylene terephthalate, polyethylene terephthalate glycol-modified, polycarbonate, polypropylene, and polyethylene, and wherein a thickness of the flexible substrate ranges from about 30 μm to about 50 82 m; and
depositing a signal amplifying material on a tip of each of the collapsible nano-pillars.

16. The method as defined in claim 15 wherein creating the mold is accomplished via electron-beam lithography or photolithography, and dry etching.

17. The method as defined in claim 15 wherein the method is performed as a roll-to-roll process.

* * * * *